US010457994B2

(12) United States Patent
Wu et al.

(10) Patent No.: US 10,457,994 B2
(45) Date of Patent: Oct. 29, 2019

(54) 4-MIRNA SIGNATURE FOR PREDICTING CLEAR CELL RENAL CELL CARCINOMA METASTASIS AND PROGNOSIS (71) Applicant: CITY OF HOPE, Duarte, CA (US)

(72) Inventors: Huiqing Wu, San Marino, CA (US); Xiwei Wu, Diamond Bar, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 15/702,681

(22) Filed: Sep. 12, 2017

(65) Prior Publication Data
US 2018/0223370 A1  Aug. 9, 2018

Related U.S. Application Data (63) Continuation of application No. 13/284,735, filed on Oct. 28, 2011, now Pat. No. 9,771,619.

(60) Provisional application No. 61/407,880, filed on Oct. 28, 2010.

(51) Int. Cl.
*C12Q 1/6886* (2018.01)
(52) U.S. Cl.
CPC ...... *C12Q 1/6886* (2013.01); *C12Q 2600/118* (2013.01); *C12Q 2600/158* (2013.01); *C12Q 2600/178* (2013.01)
(58) Field of Classification Search
CPC ............ C12Q 1/6886; C12Q 2600/118; C12Q 2600/158; C12Q 2600/178
USPC ....... 435/6.12, 91.1, 91.31; 506/7; 536/23.1, 536/24.5
See application file for complete search history.

(56) References Cited

U.S. PATENT DOCUMENTS

2009/0286242 A1  11/2009  Hannon et al.

OTHER PUBLICATIONS

Bartel DP. MicroRNAs: genomics, biogenesis, mechanism, and function. Cell. Jan. 23, 2004;116(2):281-97.
Borgdorff V, Lleonart ME, Bishop CL, Fessart D, Bergin AH, Overhoff MG, et al. Multiple microRNAs rescue from Ras-induced senescence by inhibiting p21(Waf1/Cip1). Oncogene. Apr. 15, 2010;29(15):2262-71.
Calin GA, Croce CM. MicroRNA signatures in human cancers. Nature reviews. Nov. 2006;6 (11):857-66.
Calin GA, Croce CM. MicroRNA-cancer connection: the beginning of a new tale. Cancer research. Aug. 1, 2006;66(15):7390-4.
Calin GA, Ferracin M, Cimmino A, Di Leva G, Shimizu M, Wojcik SE, et al. A MicroRNA signature associated with prognosis and progression in chronic lymphocytic leukemia. The New England journal of medicine. Oct. 27, 2005;353(17):1793-801.
Calin GA, Liu CG, Sevignani C, Ferracin M, Felli N, Dumitru CD, et al. MicroRNA profiling reveals distinct signatures in B cell chronic lymphocytic leukemias. Proceedings of the National Academy of Sciences of the United States of America. Aug. 10, 2004;101(32):11755-60.
Cervigne NK, Reis PP, Machado J, Sadikovic B, Bradley G, Galloni NN, et al. Identification of a microRNA signature associated with progression of leukoplakia to oral carcinoma. Hum Mol Genet. Dec. 15, 2009;18(24):4818-29.
Chan JA, Krichevsky AM, Kosik KS. MicroRNA-21 is an antiapoptotic factor in human glioblastoma cells. Cancer research. Jul. 15, 2005;65(14):6029-33.
Chow TF, Youssef YM, Lianidou E, Romaschin AD, Honey RJ, Stewart R, et al. Differential expression profiling of microRNAs and their potential involvement in renal cell carcinoma pathogenesis. Clin Biochem. Jan. 2010;43(1-2):150-8.
Cohen HT, McGovern FJ. Renal-cell carcinoma. The New England journal of medicine. Dec. 8, 2005;353(23):2477-90.
Coughlin, Caroline GIM. Current and emerging concepts in tumour metastasis. The Journal of pathology. 2010;222(1):1-15.
Cummins JM, Velculescu VE. Implications of micro-RNA profiling for cancer diagnosis. Oncogene. Oct. 9, 2006;25(46):6220-7.
Eis PS, Tam W, Sun L, Chadburn A, Li Z, Gomez MF, et al. Accumulation of miR-155 and BIC RNA in human B cell lymphomas. Proceedings of the National Academy of Sciences of the United States of America. Mar. 8, 2005;102(10):3627-32.
Esquela-Kerscher A, Slack FJ. Oncomirs—microRNAs with a role in cancer. Nature reviews. Apr. 2006;6(4):259-69.
Garzia L, Andolfo I, Cusanelli E, Marino N, Petrosino G, De Martino D, et al. MicroRNA—199b—5p impairs cancer stem cells through negative regulation of HES1 in edulloblastoma. PloS one. 2009;4(3):e4998.
Gee HE, Camps C, Buffa FM, Colella S, Sheldon H, Gleadle JM, et al. MicroRNA-10b and breast cancer metastasis. Nature. Oct. 23, 2008;455(7216):E8-9; author reply E.
Guo J, Miao Y, Xiao B, Huan R, Jiang Z, Meng D, et al. Differential expression of microRNA species in human gastric cancer versus non-tumorous tissues. J Gastroenterol Hepatol. Apr. 2009;24(4):652-7.
Gupta K, Miller JD, Li JZ, Russell MW, Charbonneau C. Epidemiologic and socioeconomic burden of metastatic renal cell carcinoma (mRCC): a literature review. Cancer Treat Rev. May 2008;34(3):193-205.
Han KR, Bleumer I, Pantuck AJ, Kim HL, Dorey FJ, Janzen NK, et al. Validation of an integrated staging system toward improved prognostication of patients with localized renal cell carcinoma in an international population. J Urol. Dec. 2003;170(6 Pt 1): 2221-4.

(Continued)

*Primary Examiner* — Jane J Zara
(74) *Attorney, Agent, or Firm* — Perkins Coie LLP; Lara Dueppen; Yang Tang (57) ABSTRACT

An miRNA expression signature comprising a set of one or more miRNAs associated with metastatic cancer is provided. In one embodiment, the expression signature is selected from the group consisting of miR-10b, miR-139-5p, miR-130b and miR-199b-5p. In some aspects, miR-199b-5p and miR-130b are overexpressed in metastatic cancer; and miR-10b and miR-139-5p are downregulated in metastatic cancer. Such an expression signature may be used in methods for predicting metastasis, risk for developing metastasis or a prognosis in a cancer. In another embodiment, a method for establishing such a cancer miRNA expression signature is provided.

5 Claims, 9 Drawing Sheets

(56) References Cited

OTHER PUBLICATIONS

He L, Thomson JM, Hemann MT, Hernando-Monge E, Mu D, Goodson S, et al. A microRNA polycistron as a potential human oncogene. Nature. Jun. 9, 2005;435 (7043): 828-33.

Hiroki E, Akahira J, Suzuki F, Nagase S, Ito K, Suzuki T, et al. Changes in microRNA expression levels correlate with clinicopathological features and prognoses in endometrial serous adenocarcinomas. Cancer science. Jan. 2010;101(1):241-9.

Hurst DR, Edmonds MD, Welch DR. Metastamir: the field of metastasis-regulatory microRNA is spreading. Cancer research. Oct. 1, 2009;69(19):7495-8.

Iorio MV, Ferracin M, Liu CG, Veronese A, Spizzo R, Sabbioni S, et al. MicroRNA gene expression deregulation in human breast cancer. Cancer research. Aug. 15, 2005;65 (16):7065-70.

Jiang Z, Chu PG, Woda BA, Rock KL, Liu Q, Hsieh CC, et al. Analysis of RNA-binding protein IMP3 to predict metastasis and prognosis of renal-cell carcinoma: a retrospective study. Lancet Oncol. Jul. 2006;7(7):556-64.

Jung M, Mollenkopf HJ, Grimm C, Wagner I, Albrecht M, Waller T, et al. MicroRNA profiling of clear cell renal cell cancer identifies a robust signature to define renal malignancy. Journal of cellular and molecular medicine. Sep. 2009;13(9B):3918-28.

Klein CA. Cancer. The metastasis cascade. Science. Sep. 26, 2008;321(5897):1785-7.

Landis SH, Murray T, Bolden S, Wingo PA. Cancer statistics, 1999. CA: a cancer journal for clinicians. Jan.-Feb. 1999;49(1):8-31, 1.

Liu CG. An oligonucleotide microchip for genome-wide microRNA profiling in human and mouse tissues. PNAS. Jun. 29, 2004; 101(26):9740-9744.

Ma L, Teruya-Feldstein J, Weinberg RA. Tumour invasion and metastasis initiated by microRNA-10b in breast cancer. Nature. Oct. 11, 2007;449(7163):682-8.

Metzler M, Wilda M, Busch K, Viehmann S, Borkhardt A. High expression of precursor microRNA-155/BIC RNA in children with Burkitt lymphoma. Genes, chromosomes & cancer. Feb. 2004;39(2):167-9.

Michael MZ, SM OC, van Hoist Pellekaan NG, Young GP, James RJ. Reduced accumulation of specific microRNAs in colorectal neoplasia. Mol Cancer Res. Oct. 2003;1(12):882-91.

miRNA registry for *Homo sapiens* taken from http://www.mirbase.org/cgi-bin/mirna_summary.pl?org=has on Aug. 19, 2014.

Nakada C, Matsuura K, Tsukamoto Y, Tanigawa M, Yoshimoto T, Narimatsu T, et al. Genome-wide microRNA expression profiling in renal cell carcinoma: significant down-regulation of miR-141 and miR-200c. The Journal of pathology. Dec. 2008;216 (4):418-27.

Nicoloso MS, Spizzo R, Shimizu M, Rossi S, Calin GA. MicroRNAs—the micro steering wheel of tumour metastases. Nature reviews. Apr. 2009;9(4):293-302.

Pantuck, A. J., Zisman, A., Belldegrun, A. S. The changing natural history of renal cell carcinoma. J. Urol. Nov. 2001; 166(5):1611-1623.

Patard JJ, Kim HL, Lam JS, Dorey FJ, Pantuck AJ, Zisman A, et al. Use of the University of California Los Angeles integrated staging system to predict survival in renal cell carcinoma: an international multicenter study. J Clin Oncol. Aug. 15, 2004;22(16):3316-22.

Patnaik SK, Kannisto E, Knudsen S, Yendamuri S. Evaluation of microRNA expression profiles that may predict recurrence of localized stage I non-small cell lung cancer after surgical resection. Cancer research. Jan. 1, 2010;70(1):36-45.

Peltier HJ, Latham GJ. Normalization of microRNA expression levels in quantitative RT-PCR assays: identification of suitable reference RNA targets in normal and cancerous human solid tissues. RNA (New York, NY. May 2008;14(5):844-52.

Rini BI, Campbell SC, Escudier B. Renal cell carcinoma. Lancet. Mar. 28, 2009;373 (9669): 1119-32.

Sasayama T, Nishihara M, Kondoh T, Hosoda K, Kohmura E. MicroRNA-10b is overexpressed in malignant glioma and associated with tumor invasive factors, uPAR and RhoC. International journal of cancer. Sep. 15, 2009;125(6):1407-13.

Simon R, Radmacher MD, Dobbin K, McShane LM. Pitfalls in the use of DNA microarray data for diagnostic and prognostic classification. J Natl Cancer Inst. Jan. 1, 2003;95(1):14-8.

Tian Y, Luo A, Cai Y, Su Q, Ding F, Chen H, et al. MicroRNA-10b promotes migration and invasion through KLF4 in human esophageal cancer cell lines. The Journal of biological chemistry. Mar. 12, 2010;285 (11): 7986-94.

Volinia S, Calin GA, Liu CG, Ambs S, Cimmino A, Petrocca F, et al. A microRNA expression signature of human solid tumors defines cancer gene targets. Proceedings of the National Academy of Sciences of the United States of America. Feb. 14, 2006;103 (7):2257-61.

Weinberg RA. Leaving home early: reexamination of the canonical models of tumor progression. Cancer cell. Oct. 7, 2008;14(4):283-4.

Weng L, Wu X, Gao H, Mu B, Li X, Wang JH, et al. MicroRNA profiling of clear cell renal cell carcinoma by whole-genome small RNA deep sequencing of paired frozen and formalin-fixed, paraffin-embedded tissue specimens. The Journal of pathology. 2010; 222:41-51.

Yanaihara N, Caplen N, Bowman E, Seike M, Kumamoto K, Yi M, et al. Unique microRNA molecular profiles in lung cancer diagnosis and prognosis. Cancer cell. Mar. 2006;9(3):189-98.

Yu SL, Chen HY, Chang GC, Chen CY, Chen HW, Singh S, et al. MicroRNA signature predicts survival and relapse in lung cancer. Cancer cell. Jan. 2008;13(1):48-57.

4-MIRNA SIGNATURE FOR PREDICTING CLEAR CELL RENAL CELL CARCINOMA METASTASIS AND PROGNOSIS

CROSS REFERENCE TO RELATED APPLICATIONS

This application is a continuation of U.S. application Ser. No. 13/284,735, filed Oct. 28, 2011, which claims benefit of U.S. Provisional Patent Application No. 61/407,880, filed Oct. 28, 2010, which is incorporated herein by reference in its entirety.

BACKGROUND

Renal cell carcinoma (RCC) accounts for about 3% of all malignant tumors in adults. Its worldwide incidence and mortality are approximately 209,000 and 102,000 per year respectively, including 39,000 new cases and 13,000 deaths in the United States (Gupta et al. 2008). Clear cell RCC (ccRCC) represents the most common renal cancer histology, comprising 70-80% of all RCC cases (Rini et al. 2009). About 30% of patients with newly diagnosed disease have evidence of metastases at presentation (Landis et al 1999). Once RCC has metastasized, few patients achieve a durable remission. Only about 15-25% of patients having metastatic RCC respond to currently available therapies and the overall median survival is less than one year (Gupta et al. 2008). RCC metastasis cannot be predicted reliably based on patients' clinical manifestations, pathologic findings or other currently available laboratory tests.

Although several algorithms have been used to predict clinical outcome for patients with metastatic RCC (mRCC) on the basis of clinical and pathologic features, these do not incorporate the more complex biological features of individual patients (Rini et al. 2009; Zisman et al. 2001). Recent studies have shown that the metastatic capability of cancer is conferred by genetic changes that occur relatively early in tumorigenesis and that metastatic dissemination may occur continually throughout the course of primary tumor development (Weinberg 2008; Klein 2008; Coghlin 2010).

Early detection of ccRCC metastatic potential may be beneficial for a more precise prediction of clinical outcomes and may ultimately be used to identify subsets of patients that may benefit from specific targeted therapies. Therefore, it is desired to identify metastasis-specific molecular biomarkers at the time of nephrectomy to predict ccRCC metastasis.

SUMMARY

An miRNA expression signature comprising a set of one or more miRNAs associated with metastatic cancer is provided herein. In one embodiment, the expression signature is selected from the group consisting of miR-10b, miR-139-5p, miR-130b and miR-199b-5p. In some aspects, miR-199b-5p and miR-130b are upregulated or overexpressed in metastatic cancer; and miR-10b and miR-139-5p are downregulated or underexpressed in metastatic cancer.

In another embodiment, a method for establishing such a cancer miRNA expression signature is provided. The method includes determining a plurality of miRNA expression levels in one or more tumor tissue samples from a cohort of subjects; performing a univariate logistic regression analysis to identify a set of one or more miRNAs associated with metastasis; assigning a risk score to each tumor tissue sample by calculating a risk score formula; and determining a cut-off risk score to stratify the cohort subjects into one or more risk groups: low risk or high risk. In some embodiments, the miRNA expression levels may be determined by microarray analysis or RT-PCR. In other embodiments, the one or more miRNAs are selected from the group consisting of miR-10b, miR-139-5p, miR-130b and miR-199b-5p.

In another embodiment, a method for predicting existence of or risk for developing metastasis is provided. The method includes detecting a test expression level of a set of one or more miRNAs of a cancer-specific expression signature in a biological test sample from a subject having a cancer such as clear cell renal cell carcinoma; assigning a risk score to the test expression level; and predicting the existence of or a high risk for developing metastasis when the test expression level is assigned a high risk score, predicting a low risk for developing metastasis when the test expression level is assigned a low risk score. In some embodiments, the miRNA expression levels may be determined by microarray or RT-PCR. In other embodiments, the one or more miRNAs are selected from the group consisting of miR-10b, miR-139-5p, miR-130b and miR-199b-5p.

A method for predicting a prognosis in a cancer patient is provided. The method includes detecting a test expression level of a set of one or more miRNAs of a cancer-specific expression signature in a biological test sample from a subject having a cancer such as clear cell renal cell carcinoma; assigning a risk score to the test expression level; and predicting the a poor prognosis when the test expression level is assigned a high risk score; and predicting a good prognosis when the test expression level is assigned a low risk score. In some embodiments, the miRNA expression levels may be determined by microarray or RT-PCR. In other embodiments, the one or more miRNAs are selected from the group consisting of miR-10b, miR-139-5p, miR-130b and miR-199b-5p.

DETAILED DESCRIPTION

A microRNA (miRNA) expression signature that may be used as a basis for computational methods or algorithms used for prediction, prognosis, screening, early diagnosis, staging, therapy selection and monitoring of a cancer and cancer related metastases is provided. In one embodiment, the miRNA expression signature includes an expression profile of one or more miRNA molecules. In one aspect, the miRNA molecules are selected from miR-10b, miR-130b, miR-139-5p and miR-199b-5p.

According to the embodiments described herein, an miRNA expression signature and methods for its use may be generated toward any organ-specific cancer. In one embodiment, the miRNA expression signature is specific to clear cell renal cell carcinoma (ccRCC).

An "expression signature" is a group two or more genes or gene-related molecules (e.g., DNA, RNA, amino acids and proteins) that exist in a cell, tissue fluid or other sample whose combined expression pattern is characteristic of a particular tissue or is characteristic of a particular condition, or disease state. The expression signature can be used to select or stratify a group of subjects based on, for example, a specific stage of a disease, a risk of developing a particular disease or state of disease or a probability or prediction of a prognosis, with sufficient accuracy to facilitate diagnosis or selection of treatment.

MicroRNA (miRNA) is a group of small non-coding RNAs that regulate gene expression during development and differentiation (Bartel 2004). miRNA expression is very tissue-specific (Bartel 2004). Some miRNAs that are stably expressed in certain tissue types might be expressed differently in other tissue types. In some embodiments, the miRNA molecules are present in tissues and/or organs at normal physiological conditions, but may be expressed at a much higher or lower level in diseased tissue or cells and are indicative of a change in health status. In other embodiments, the biomarkers may be absent in tissues and/or organs under normal physiological conditions, but are specifically expressed in diseased tissue or cells. In other embodiments, the biomarkers may be specifically released to the bloodstream under conditions of ccRCC, and/or are over- or under-expressed as compared to normal levels. Measurement of miRNA, alone or in combination, in patient samples provides information that may correlate with a diagnosis of the selected disease. Therefore, a set of one or more miRNA molecules may be used in diagnostic and prognostic assays.

As used herein the phrase "diagnostic" or means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay may be termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As used herein the phrase "diagnosing" refers to classifying a disease or a symptom, determining a severity of the disease, monitoring disease progression, forecasting an outcome of a disease and/or prospects of recovery. The term "detecting" may also optionally encompass any of the above.

A "prognosis" may be measured as any outcome of illness. In some embodiments a prognosis is a measurement of or prediction of overall survival, recurrence-free survival, or progression of a disease. A good prognosis indicates, for example, that the disease is less likely to progress, the chance of survival after diagnosis or treatment is high or the length of time a subject is likely to live after diagnosis or after treatment is a relatively long period of time. A poor prognosis indicates, for example, that the disease is more likely to progress, the chance of survival after diagnosis or treatment is low or the length of time a subject is likely to live after diagnosis or after treatment is relatively short.

Alteration of miRNA expression has been shown in malignancies (Michael et al. 2003; Calin et al. 2005; Yanaihara et al. 2006) and plays an important role in tumorigenesis and cancer progression (Esquela-Kerscher & Slack 2006). Studies have shown that certain miRNAs play important roles in various steps of the metastatic cascade, such as the endothelial-mesenchymal transition (EMT), adhesion, migration, invasion, apoptosis and angiogenesis. Because the expression of multiple genes can be regulated by a single miRNA, miRNA expression profiles may be more accurate in determining cancer subtypes than RNA profiles of protein-coding genes (Calin & Croce 2006; Volinia et al. 2006). Expression signatures based on miRNA expression have been shown to aid in diagnosis and prognostication of cancer (Yu et al. 2008; Hiroki et al. 2010).

In the current study, miRNA expression levels in benign kidney and ccRCC specimens were profiled using microarray. miRNA expression levels may also be profiled using a PCR-based assay, as further discussed herein. The miRNA expression associated with metastasis in a training cohort was analyzed to develop a 4-miRNA expression signature model that can predict concurrent and potential ccRCC metastasis and cancer-specific survival. This expression signature has been validated in an independent testing cohort and has also been converted to a quantitative PCR (q-PCR)-based assay, which may be used to validate large clinical cohorts and has the potential to be applied in a routine clinical setting.

In one embodiment, a method for generating an miRNA expression signature is provided. Such a method includes detecting the expression of miRNA in one or more tumor tissue samples from a cohort of subjects. In one embodiment, the cohort of subjects includes a group of subjects having a representative tumors at each AJCC stage (I, II, III, IV). The miRNA expression may be detected by any suitable method for RNA detection including, but not limited to, microarray, reverse transcriptase polymerase chain reaction (RT-PCR) or other PCR-based assays (e.g. quantitative or real time RT-PCR) or mass spectrometry.

The method for generating an miRNA expression signature further comprises performing a univariate logistic regression analysis to identify a set of one or more miRNAs associated with metastases. In one embodiment, the set of one or more miRNAs are selected from miR-10b, miR-130b, miR-139-5p and miR-199b-5p. The studies discussed below show that miR-199b-5p and miR-130b are overexpressed in ccRCC metastatic cancer; and miR-10b and miR-139-5p are downregulated in metastatic cancer ccRCC. These miRNAs have been shown to be relevant to other cancers as well. MiR-139-5p has been shown to be downregulated in endometrial serous and gastric adenocarcinoma (Hiroki et al. 2010; Guo et al 2009). Overexpression of miR-130b is involved in the growth control of breast epithelial cells via the modulation of the cell cycle inhibitor $p21^{Waf1/Cip\ 1}$ (Borgdorff et al. 2010). Altered expression of miR-199b-5p involves HES-1 gene regulation and is associated with metastatic spread of medulloblastoma (Garzia et al. 2009). Dysregulation of miR-10b has been found in malignant glial tumors, esophageal cancer cell lines and primary breast cancer, though whether it is present in breast metastasis is in debate (Sasayama et al. 2009; Tian et al. 2010; Iorio et al. 2005; Ma et al. 2007; Gee et al. 2008).

The method for generating an miRNA expression signature may also include a step assigning a risk score to each tumor tissue sample by calculating a risk score formula and determining a cut-off risk score to stratify the cohort subjects into one or more risk groups (e.g., high risk, low risk, intermediate risk) as described in further detail in the examples below.

In other embodiments, methods for predicting a cancer prognosis, the existence of metastasis or the risk for developing metastasis are provided. These methods may include detecting a test expression level of one or more miRNAs as part of a cancer-specific expression signature in a biological sample from a subject having a cancer, assigning a risk score to the test expression level; and predicting a cancer prognosis, the existence of metastasis or the risk for developing metastasis.

When the test expression level is assigned a high risk score, the subject likely has metastasis or is likely to have metastasis. A high risk score may also be indicative of a poor prognosis. When the test expression level is assigned a low risk score, the subject is likely to be at low risk for having or developing metastasis. A low risk score may also be indicative of a good prognosis.

As further described in the examples below, an independent testing cohort was validated and showed that the 4-miRNA expression signature described above exhibits high sensitivity and specificity for predicting metastasis. Currently, there is no clinically available molecular assay to predict ccRCC metastasis. A retrospective study previously reported that IMP3 expression analysis by immunohistochemistry could predict RCC metastasis and prognosis (Jiang et al. 2006). The retrospective study identified IMP-positive tumors were identified in 59/95 metastatic RCCs, 60/119 primary RCCs with metastasis and 11/287 primary RCCs with no metastasis. This resulted in an overall sensitivity of 56%, a specificity of 96% and a hazard ratio of 5.66. The 4-miRNA expression signature described herein achieves a higher sensitivity (75%), specificity (100%) and hazard ratio (12.68) as compared to the IMP3 study.

In some embodiments, the methods of the present invention provide for utilizing a biological sample of a subject or patient received from a third party; or obtaining a biological sample from a subject or a patient. Examples of suitable biological samples which may optionally be used with the embodiments of the present invention include but are not limited to blood, serum, plasma, blood cells, urine, sputum, saliva, stool, spinal fluid or CSF, lymph fluid, the external secretions of the skin, respiratory, intestinal, and genitourinary tracts, tears, milk, neuronal tissue, lung tissue, any human organ or tissue, including any tumor or normal tissue, any sample obtained by lavage (for example of the bronchial system or of the breast ductal system), and also samples of in vivo cell culture constituents. The sample can optionally be diluted with a suitable eluant before contacting the sample to an antibody and/or performing any other diagnostic assay.

Numerous well known tissue or fluid collection methods can be utilized to collect a biological sample from the subject in order to determine the level of DNA, RNA and/or polypeptide of the variant of interest in the subject. Examples include, but are not limited to, fine needle biopsy, needle biopsy, core needle biopsy and surgical biopsy (e.g., brain biopsy), and lavage. Regardless of the procedure employed or where the biopsy or sample is obtained, the level of the variant can be determined and a diagnosis can thus be made.

Having described the invention with reference to the embodiments and illustrative examples, those in the art may appreciate modifications to the invention as described and illustrated that do not depart from the spirit and scope of the invention as disclosed in the specification. The Examples are set forth to aid in understanding the invention but are not intended to, and should not be construed to limit its scope in any way. The examples do not include detailed descriptions of conventional methods. Such methods are well known to those of ordinary skill in the art and are described in numerous publications. Further, all references cited above and in the examples below are hereby incorporated by reference in their entirety, as if fully set forth herein.

Example 1: Development of a 4-miRNA Expression Signature Model for Detection of Clear Cell Renal Cell Carcinoma Metastasis Materials and Methods
Tissue Preparation and RNA Extraction.

A total of 78 frozen benign kidney and clear cell renal cell carcinoma (ccRCC) specimens were used for the study. All the samples were collected from nephrectomy specimens of ccRCC patients at the City of Hope (COH) National Medical Center between 1986 and 2009. The samples were snap-frozen shortly after nephrectomy and had been stored at −80° C. at the COH Tumor Bank since collected. Formalin-fixed paraffin embedded (FFPE) samples may also be used for the miRNA expression profiling studies (Weng et al. 2010). The protocol for using these samples was approved by the COH Cancer Protocol Review and Monitoring Committee (CPRMC) and Institutional Review Board (IRB). Total RNA was extracted from up to 10 sections (10 μm in thickness) of each sample as described previously (Weng et al. 2010).

Microarray Analysis for miRNA.

Microarray testing of miRNA expression was performed at the COH Microarray Core using the MicroRNA Human Version 2 Microarray (probes for 723 human, Sanger miRBase 10.1) (Agilent Technologies, Inc., Santa Clara Calif.), as described previously (Weng et al. 2010).

Statistical Analysis.

The analysis was performed using R statistical language. Raw data from Agilent miRNA array was processed by Quantile normalization, followed by a log 2 transformation with an offset of 1. miRNAs with a log 2 normalized expression level that is greater than 8 or called "absent" by Agilent's Feature Extraction software in more than 90% of the samples were discarded. Differentially expressed miRNAs between tumor (training cohort) and benign samples were selected using t-test with a p value ≤0.05 and a 2-fold change. The miRNA expression signature was developed using the following steps. First, univariate logistic regression analysis was used to identify miRNAs that were associated with metastasis. Second, a mathematical formula based on the expression levels of the above identified miRNAs was developed to assign a risk score for each patient. Third, a risk score cut-off level was determined to classify each patient into a high or low risk group. The first step is a feature selection step. The second and third steps are model building steps.

For the first step, a range of p values (0.05, 0.02, 0.01, 0.005, 0.002 and 0.001) were tested with Leave-One-Out Cross Validation (LOOCV) and the best p value cutoff score was found to be 0.01. Specifically, at each iteration step of the cross validation, one test sample was tested (the test sample) while the others remained in the training group (n=28-1). During this process, the feature selection and formula development were repeated within each iteration step and the expression signature model was used to predict the status of the test sample. The feature selection and expression signature model building steps were entirely independent of the test sample. This is important to ensure that the performance of the expression signature model formula developed can be estimated without bias. Using LOOCV, a minimal error rate was achieved having a p value of <0.01. A 2 or more-fold-change between metastatic and localized specimens was required to help develop a PCR-based assay for the expression signature. These criteria resulted in 4 miRNAs that were significantly associated with metastasis.

To investigate the effectiveness of these four miRNAs as an expression signature to predict metastasis, a mathematical formula was constructed, taking into account both the strength and the positive or negative association of each miRNA with metastasis. More specifically, a risk score for each patient in the training cohort group was calculated using the formula, which was a linear combination of the expression level of the miRNAs, weighted by the regression coefficients derived from the aforementioned univariate logistic regression analysis. To choose the optimal risk score cutoff, a range of scores were tested to stratify these patients into high and low risk groups. The false positive rate (FPR) and true positive rate (TPR) of these cutoffs were calculated and a risk score cutoff point was selected based on the lowest FPR and highest TPR (FPR=8%, TPR=100%, FIG. 5). Therefore, an miRNA expression signature model, which consists of a risk score formula and a high risk score cutoff, was developed to classify patients into high and low risk groups for developing metastasis.

The performance of the expression signature was further validated using the additional independent testing cohort data set (n=40), in which each patient's risk for developing metastasis was determined based on the calculated risk score and then compared to the clinical follow-up information. To investigate whether the 4-miRNA expression signature was also an independent prognostic factor for cancer specific survival, univariate Cox regression analysis was used to examine the patients' risk status based on the expression signature, patient age and gender, tumor histologic grade and size, clinical stage and available UCLA Integrated Staging System (UISS) score (see discussion below). A p value of <0.05 was used to determine significance.

Reverse Transcriptase Polymerase Chain Reaction (RT-PCR).

In each sample, the expression of each of the 4-miRNAs (hsa-miR-10b, 130b, 139-5p and 199b-5p) was analyzed using RT-PCR TaqMan MicroRNA Assays and 7900HT Fast Real-time PCR System (Applied Biosystems, Carlsbad, Calif.). Briefly, 10 ng of total RNA from each sample was subjected to reverse-transcription forming $1_{st}$ strand cDNA with mature miRNAs specific primers containing stem loop, followed by real-time PCR with TaqMan probes. PCR reactions for each sample were carried out in triplicate. Each miRNA expression, normalized by hsa-miR-24, was quantified using the following formula: $X=2^{-\Delta CT}$, where $\Delta C_{T(miR-X)} - C_{T(miR-24)}$.

Clinical Characterization of Patients' Specimens in the Training and Testing Cohorts A set of benign kidney specimens as control samples (n=10) and a 28-sample ccRCC training cohort including localized/stage I (pT1, n=13) and metastatic (M1, n=15) tumors were used to profile miRNA expression in ccRCC and to develop a metastasis-specific expression signature. In addition, an independent ccRCC testing cohort was used to validate the expression signature, which included 40 primary tumor specimens of stage I (pT1, n=6), II (pT2, n=6), III (pT3, n=17) and IV (N2 or M1, n=11) tumors. In the testing cohort, the majority (34/40) of the specimens had at least 5 year follow-up information if there was no metastasis reported. The clinical characteristics of the specimens are summarized in Table 1 below.

TABLE 1

Clinical characteristics of patients and tumor specimens (n = 68) in the training and testing cohorts.

| | | Training cohort numbers (%) | Testing cohort numbers (%) |
|---|---|---|---|
| Patients/specimens | | 28 | 40 |
| Age | (mean ± SD) | 62.4 ± 13.7 | 57.4 ± 12.0 |
| Gender | Male | 15 (53 · 6) | 24 (60 · 0) |
| | Female | 13 (46 · 4) | 16 (40 · 0) |
| Grade* | I | 1 (7.7) | 0 (0.0) |
| | II | 8 (61.5) | 12 (30.0) |
| | III | 3 (23.1) | 15 (37.5) |
| | IV | 1 (7.7) | 13 (32.5) |
| Stage | I | 13 (46.4) | 6 (15.0) |
| | II | 0 (0.0) | 6 (15.0) |
| | III | 0 (0.0) | 17 (42.5) |
| | IV | 15 (53.6) | 11 (27.5) |
| Size* | (mean ± SD) | 3.4 ± 1.1 | 9.1 ± 4.0 |

*The tumor grade and size are only applied to the primary tumors (n = 53).

Profiling of miRNA Expression in ccRCCs

Figure 1:
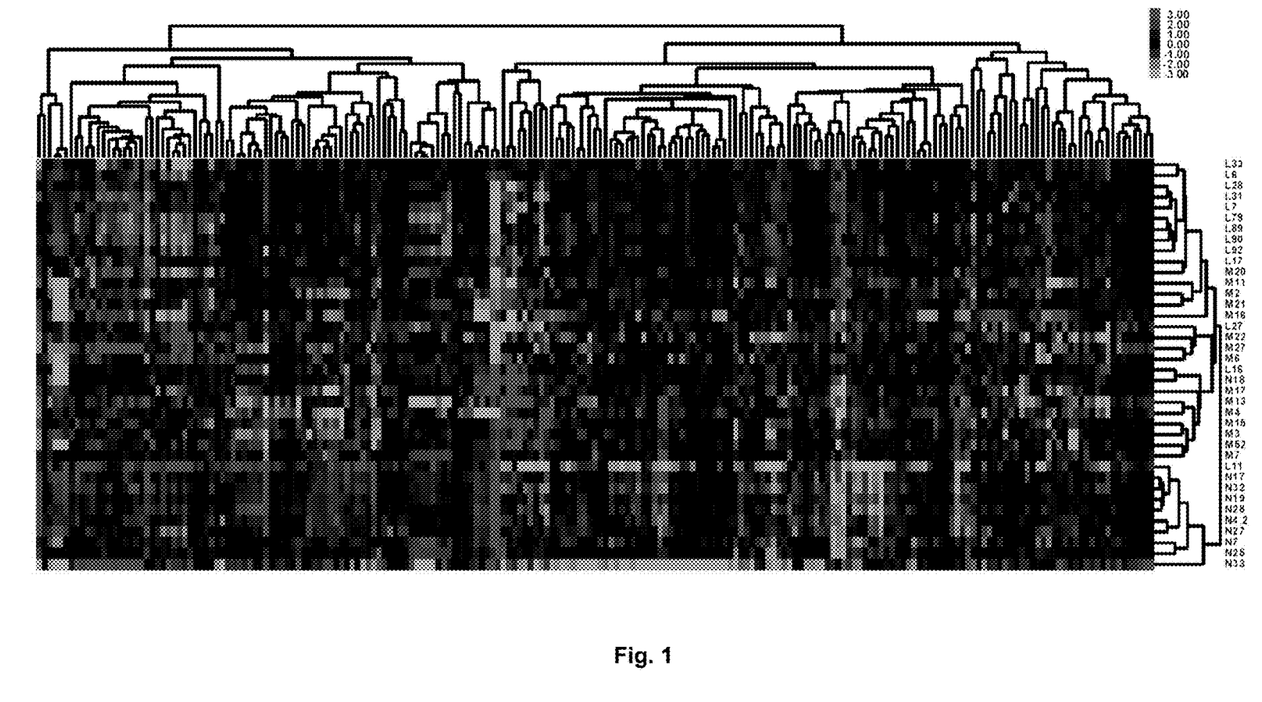
FIG. 1 illustrates an unsupervised hierarchical clustering of miRNA expression levels using benign kidney and clear cell renal cell carcinoma (ccRCC) specimens. The miRNA expression levels were measured using the Agilent microarray technology with Quantile normalization and then filtered as described (see Material and methods). The transformed log 2 intensities were mean centered across samples and a hierarchical clustering with average linkage was conducted with Cluster v3.0 and visualized with Java Treeview v1.1.3. (N-: benign kidney tissue; L-: T1 ccRCC specimen; M-: metastatic ccRCC specimen.)
Figure 2A:
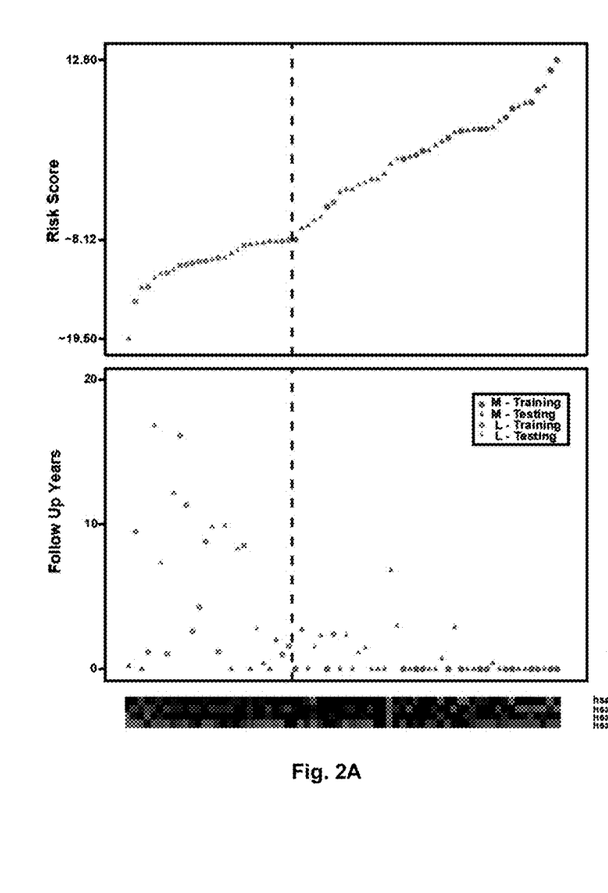
FIGS. 2A-B are a clear cell renal cell carcinoma (ccRCC) metastasis-specific miRNA expression signature developed using microarray (FIG. 2A) and quantitative PCR (qPCR) (FIG. 2B). The risk score distribution (upper panel), survival status (middle panel) and expression profiles of the four miRNAs for all 68 ccRCC patients in the training and testing cohort are shown. The dotted line represents the signature cut-off score to stratify patients into low and high risk groups. (M: metastatic patient; L: patient with no history of metastasis; Training: training cohort patient; Testing: testing cohort patient.)
Figure 2B:
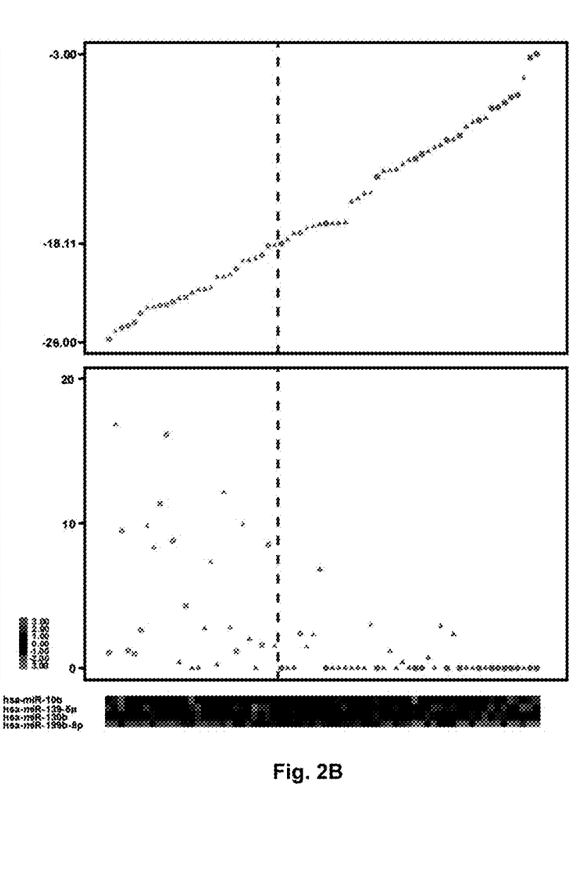

Using Agilent microarray technology, the miRNA expression of the benign kidney samples (n=10) and the training cohort specimens (n=28) was profiled (FIG. 1). As shown in FIGS. 2A-B, an unsupervised hierarchical clustering using these miRNA expression data separated the benign and tumor samples. With a cut-off score of a 2-fold change and an FDR 0.05, 56 miRNAs were found to be aberrantly expressed in ccRCCs; 29 were up-regulated and 27 were down-regulated as shown in Table 3 below. Within the tumor group, 21 miRNAs were found to be differentially expressed between localized and metastatic specimens; 7 were upregulated and 14 were down-regulated in the metastatic tumors as shown in Table 3 below.

TABLE 2

Differentially expressed miRNAs in clear cell renal cell carcinoma compared to benign kidney tissue (n = 38)

| miRNA ID | Benign | Tumor | Log2 ratio | P value | FDR |
| --- | --- | --- | --- | --- | --- |
| hsa-miR-200c | 11.03 | 6.91 | −4.12 | 2.00E−05 | 3.76E−04 |
| hsa-miR-141 | 12.90 | 8.81 | −4.10 | 9.00E−05 | 8.87E−04 |
| hsa-miR-122 | 3.03 | 6.90 | 3.87 | 9.00E−05 | 8.87E−04 |
| hsa-miR-210 | 9.11 | 12.62 | 3.51 | 0.00E+00 | 0.00E+00 |
| hsa-miR-514 | 6.71 | 3.72 | −2.99 | 1.00E−03 | 5.05E−03 |
| hsa-miR-224 | 5.02 | 7.98 | 2.96 | 1.00E−05 | 2.59E−04 |
| hsa-miR-204 | 13.15 | 10.39 | −2.77 | 7.64E−05 | 2.77E−02 |
| hsa-miR-138 | 6.41 | 3.92 | −2.49 | 7.80E−04 | 4.04E−03 |
| hsa-miR-885-5p | 3.87 | 6.22 | 2.35 | 1.34E−03 | 6.30E−03 |
| hsa-miR-34b* | 7.40 | 9.58 | 2.18 | 2.00E−05 | 3.76E−04 |
| hsa-miR-30a* | 12.89 | 10.73 | −2.17 | 2.00E−05 | 3.76E−04 |
| hsa-miR-7 | 5.07 | 7.17 | 2.11 | 5.00E−05 | 6.47E−04 |
| hsa-miR-429 | 11.60 | 9.54 | −2.06 | 2.60E−04 | 1.93E−03 |
| hsa-miR-155 | 7.82 | 9.88 | 2.06 | 1.03E−03 | 5.08E−03 |
| hsa-miR-144* | 4.48 | 6.45 | 1.98 | 1.10E−02 | 3.55E−02 |
| hsa-miR-142-5p | 8.97 | 10.83 | 1.87 | 1.39E−02 | 4.20E−02 |
| hsa-miR-30a | 16.05 | 14.21 | −1.85 | 4.00E−05 | 5.91E−04 |
| hsa-miR-124 | 6.37 | 4.53 | −1.84 | 1.17E−02 | 3.71E−02 |
| hsa-miR-200b | 13.19 | 11.36 | −1.83 | 3.20E−04 | 2.07E−03 |
| hsa-miR-454 | 5.91 | 7.72 | 1.81 | 2.80E−04 | 1.93E−03 |
| hsa-miR-142-3p | 11.64 | 13.43 | 1.80 | 7.61E−03 | 2.77E−02 |
| hsa-miR-200a | 12.37 | 10.67 | −1.71 | 7.10E−04 | 3.93E−03 |
| hsa-miR-939 | 10.18 | 8.50 | −1.68 | 3.10E−03 | 2.07E−02 |
| hsa-miR-886-3p | 10.28 | 11.90 | 1.62 | 2.86E−03 | 1.21E−02 |
| hsa-miR-130b | 7.62 | 9.22 | 1.60 | 3.00E−05 | 5.18E−04 |
| hsa-miR-532-3p | 9.09 | 7.51 | −1.58 | 1.20E−04 | 1.08E−03 |
| hsa-miR-18a | 6.10 | 7.69 | 1.58 | 7.40E−04 | 3.93E−03 |
| hsa-miR-34a | 11.76 | 13.3 | 1.54 | 0.00E+00 | 0.00E+00 |
| hsa-miR-590-5p | 7.57 | 9.11 | 1.54 | 3.60E−04 | 2.26E−03 |
| hsa-miR-30c-2* | 8.85 | 7.33 | −1.52 | 7.40E−04 | 3.93E−03 |
| hsa-miR-532-5p | 10.40 | 8.91 | −1.49 | 0.00E+00 | 0.00E+00 |
| hsa-miR-340 | 7.24 | 8.72 | 1.49 | 2.60E−04 | 1.93E−03 |
| hsa-miR-30c | 13.59 | 12.12 | −1.47 | 1.00E−05 | 2.59E−04 |
| hsa-miR-30e* | 10.83 | 9.43 | −1.41 | 0.00E+00 | 0.00E+00 |
| hsa-miR-139-5p | 8.09 | 6.69 | −1.40 | 9.06E−03 | 3.07E−02 |
| hsa-miR-125a-3p | 9.13 | 7.74 | −1.39 | 1.19E−03 | 5.73E−03 |
| kshv-miR-K12-3 | 10.17 | 8.79 | −1.38 | 7.58E−03 | 2.77E−02 |
| hsa-miR-30d | 12.90 | 11.54 | −1.36 | 5.40E−04 | 3.19E−03 |
| hsa-miR-363 | 9.84 | 8.49 | −1.35 | 6.00E−04 | 3.45E−03 |
| hsa-miR-214 | 10.26 | 9.00 | −1.26 | 1.27E−02 | 3.97E−02 |
| hsa-miR-16 | 13.19 | 14.41 | 1.22 | 9.00E−05 | 8.87E−04 |
| hsa-miR-10b* | 7.85 | 6.63 | −1.22 | 7.08E−03 | 2.77E−02 |
| hsa-miR-362-5p | 9.52 | 8.30 | −1.21 | 1.60E−03 | 1.38E−03 |
| hsa-miR-374a | 9.65 | 10.86 | 1.21 | 8.28E−03 | 2.91E−02 |
| hsa-miR-301a | 8.63 | 9.80 | 1.17 | 1.60E−02 | 4.65E−02 |
| hsa-miR-106b | 11.72 | 12.86 | 1.15 | 1.00E−05 | 2.59E−04 |
| hsa-miR-15a | 12.38 | 13.53 | 1.15 | 4.00E−05 | 5.91E−04 |
| hsa-miR-128 | 7.68 | 8.83 | 1.15 | 3.45E−03 | 1.40E−02 |
| hsa-miR-93 | 9.72 | 10.86 | 1.14 | 8.00E−05 | 8.87E−04 |
| hsa-miR-148a | 11.14 | 12.27 | 1.13 | 2.59E−03 | 1.14E−02 |
| hsa-miR-452 | 6.40 | 7.52 | 1.12 | 7.61E−03 | 2.77E−02 |
| hsa-miR-425 | 8.22 | 9.32 | 1.10 | 8.00E−05 | 8.87E−04 |
| hsa-miR-21 | 15.87 | 16.98 | 1.10 | 1.98E−03 | 9.11E−03 |
| hsa-miR-663 | 7.37 | 6.27 | −1.09 | 1.63E−02 | 4.69E−02 |
| hsa-miR-15b | 11.68 | 12.72 | 1.04 | 2.80E−04 | 1.93E−03 |
| hsa-miR-23b | 14.44 | 13.40 | −1.03 | 1.80E−04 | 1.49E−03 |

Tumor: clear cell renal cell carcinoma.

TABLE 3

Differentially expressed miRNAs in metastatic clear cell renal cell carcinoma compared to localized tumor (n = 28).

| miRNA ID | Localized | Metastatic | Log2 ratio | P value | FDR |
| --- | --- | --- | --- | --- | --- |
| hsa-miR-199b-5p | 5.92 | 9.85 | 3.92 | 0.00E+00 | 0.00E+00 |
| hsa-miR-204 | 12.04 | 8.95 | −3.09 | 1.21E−03 | 1.57E−02 |
| hsa-miR-489 | 8.25 | 5.84 | −2.40 | 6.90E−04 | 1.02E−02 |
| hsa-miR-139-5p | 7.93 | 5.62 | −2.30 | 0.00E+00 | 0.00E+00 |
| hsa-miR-9* | 4.17 | 6.26 | 2.09 | 6.69E−03 | 4.78E−02 |
| hsa-miR-885-5p | 7.31 | 5.27 | −2.04 | 2.09E−03 | 1.98E−02 |
| hsa-miR-10b* | 7.53 | 5.85 | −1.68 | 2.00E−05 | 1.38E−03 |
| hsa-miR-10b | 13.18 | 11.58 | −1.60 | 3.20E−04 | 7.45E−03 |
| hsa-miR-483-5p | 6.61 | 8.14 | 1.54 | 1.75E−03 | 1.81E−02 |
| hsa-miR-650 | 4.42 | 5.96 | 1.54 | 7.47E−03 | 4.87E−02 |
| hsa-miR-575 | 8.25 | 9.77 | 1.52 | 2.10E−03 | 1.98E−02 |
| hsa-miR-30c-2* | 8.15 | 6.63 | −1.51 | 1.00E−04 | 4.14E−03 |
| hsa-miR-30a* | 11.51 | 10.05 | −1.46 | 5.50E−04 | 8.76E−03 |
| hsa-miR-145 | 12.45 | 11.11 | −1.34 | 3.87E−03 | 3.20E−02 |
| hsa-miR-24-1* | 7.82 | 6.49 | −1.33 | 2.57E−03 | 2.31E−02 |
| hsa-miR-200a | 11.32 | 10.10 | −1.23 | 7.76E−03 | 4.87E−02 |
| hsa-miR-455-5p | 9.04 | 7.84 | −1.20 | 3.24E−03 | 2.79E−02 |
| hsa-miR-130b | 8.61 | 9.75 | 1.14 | 4.20E−04 | 7.76E−03 |
| hsa-miR-145* | 8.04 | 6.90 | −1.14 | 5.96E−03 | 4.41E−02 |
| hsa-miR-150* | 5.85 | 6.96 | 1.11 | 4.55E−03 | 3.62E−02 |
| hsa-miR-30a | 14.77 | 13.72 | −1.05 | 7.77E−03 | 4.87E−02 |

Developing a 4-miRNA Expression Signature Model for Detection of ccRCC Metastasis.

Patients with stage I (T1) ccRCC usually have a favorable clinical outcome and their 5-year survival reaches 95% post nephrectomy (Cohen & McGovern 2005). In the study described herein, T1 tumors were considered to be "good" tumors and were used to represent the control samples to compare with the metastatic ccRCCs. Using a univariate logistic regression test and LOOCV within the training set, the optimal p value cut-off score to select the miRNAs associated with metastasis was determined. A range of p values were tested in this LOOCV test and the p value <0.01 was determined because it had the best performance among all the p value cutoff scores tested. Additionally, a 2-fold change difference between the miRNA expression in metastatic and localized tumors was used to identify all the miRNAs that showed the largest difference between metastatic and local tumors. Four miRNAs (miR-10b, miR-139-5p, miR-130b and miR-199b-5p) satisfied the above criteria, and were selected to build a metastatic tumor expression signature. MiR-199b-5p and miR-130b were over-expressed in metastatic tumors, while miR-10b and miR-139-5p were downregulated (FIG. 2A).

A risk score method was used to construct a expression signature model for ccRCC metastasis (Yu et al. 2008). The risk score formula is a linear combination of the expression levels of all the 4 miRNAs, weighted by the regression coefficients derived from the univariate logistic regression analysis, which is described as following:

$$\text{Risk score} = -1.275564 \times X_{miR-10b} + 2.106701 \times X_{miR-130b} - 2.278192 \times X_{miR-139-5p} + 1.101139 \times X_{miR-199b-5p}$$

Figure 5:
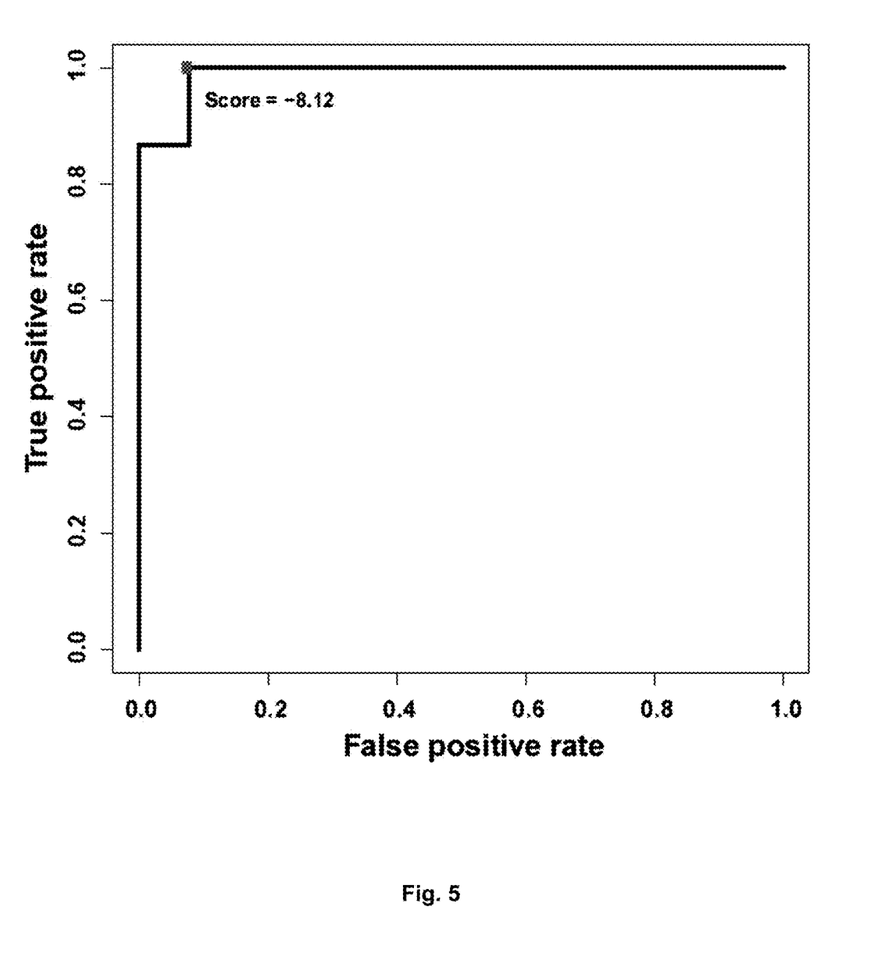
FIG. 5 is a ROC curve of miRNA risk scores using microarray training data set. The red dot indicates the selected cutoff score of −8.12, which achieves the highest true positive rate (100%) and lowest false positive rate (92%).

The next step was to determine a cut-off score for the risk score to stratify patients into a group of high or low risk for ccRCC metastasis. The risk score of each patient in the training set was calculated using the expression signature model developed, and the FPR and TPR within a range of cut-off scores were computed. A cut-off score of −8.12 was selected because it gave the best FPR and TPR (FIG. 5). Therefore, a 4-miRNA expression signature model was developed to determine the risk of tumor metastasis, in which a score ≥−8.12 indicates a high risk.

Example 2: The 4-miRNA Expression Signature Predicts Metastasis or Risk for Developing Metastasis Validation of the 4-miRNA Expression Signature in an Additional Independent Testing Cohort.

Figure 3A:
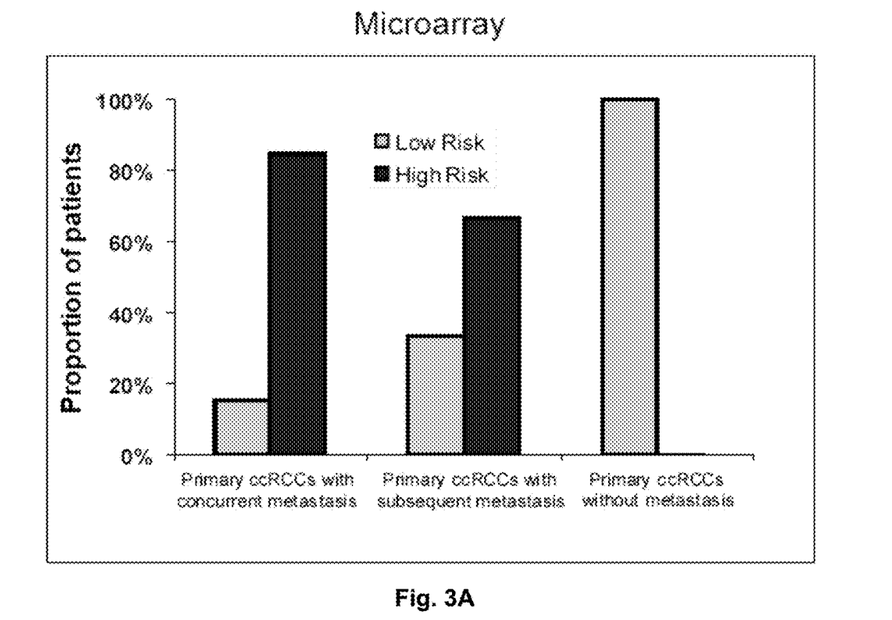
FIGS. 3A-B illustrates a 4-miRNA signature to predict high or low risk for metastasis using primary clear cell renal cell carcinoma (ccRCC) specimens in patients with concurrent (n=13), subsequent (n=15) and no (n=6) metastasis. All the patients had been followed up for at least 5 years if no metastatic diseases reported. The signature was developed based on microarray (FIG. 3A) or quantitative PCR (qPCR) (FIG. 3B) data set.

To validate the expression signature, an additional independent testing cohort containing 40 primary ccRCC specimens of different clinical stages were used. 34 of 40 (34/40) specimens had at least 5 years of follow-up information if no metastasis was reported. Each specimen was predicted to be either high or low risk based on its calculated risk score using the 4-miRNA expression signature. The predicted risk status for each patient was then compared to clinical outcome. Among the 34 samples with 5-year follow-up information, 11 of 13 (85%) primary tumors with concurrent metastasis and 10 of 15 (67%) localized tumors with subsequent metastasis were predicted to be high risk, and 6 of 6 (100%) without metastasis were predicted to be low risk (FIG. 3A). The expression signature showed an overall sensitivity of 75% (21/28) and a specificity of 100% (6/6) for the determination and prediction of metastasis. In the additional 6 primary ccRCC specimens, 1 (1/6) was predicted to be low risk and 5 (5/6) were predicted to be high risk. However, these specimens were obtained within the last two years, and future development of metastasis is not known. All 5 patients predicted to be high risk had stage III disease and the 1 patient predicted to be low risk was stage I disease. The risk score of each ccRCC specimen determined by the 4-miRNA expression signature model appeared to be the only factor significantly associated with concurrent or potential metastasis (OR=4.20, 95% CI=1.00-17.57, p<0.05). Other variables, such as a patient's gender, age, tumor grade and stage, were not useful in predicting metastasis as shown in Table 4 below.

TABLE 4

Relative odds for patients with metastasis associated with the risk score, patient's age and gender, tumor grade and size, and clinical stage in the testing cohort (n = 40).

|  | Met | Non-met | OR | 95% CI | P value |
|---|---|---|---|---|---|
| Risk Score Microarray |  |  |  |  |  |
| Score ≤−8.12 | 7 | 7 | — | — | — |
| Otherwise | 21 | 5 | 4.20 | 1.00-17.57 | 0.049 |
| Quantitative PCR |  |  |  |  |  |
| Score ≤−18.11 | 7 | 8 | — | — | — |
| Otherwise | 21 | 4 | 6.00 | 1.37-26.20 | 0.02 |
| Age |  |  |  |  |  |
| ≤50 | 8 | 2 | — | — | — |
| 51-60 | 7 | 5 | 0.35 | 0.05-2.41 | 0.29 |
| 61-70 | 9 | 3 | 0.75 | 0.10-5.69 | 0.78 |
| >70 | 4 | 2 | 0.50 | 0.05-4.98 | 0.55 |
| Age (continuous) |  |  | 0.99 | 0.93-1.05 | 0.67 |
| Gender |  |  |  |  |  |
| Female | 10 | 6 | — | — | — |
| Male | 18 | 6 | 1.80 | 0.46-7.09 | 0.40 |
| Grade |  |  |  |  |  |
| II | 6 | 6 | — | — | — |
| III | 11 | 4 | 2.75 | 0.55-13.75 | 0.22 |
| IV | 11 | 2 | 5.50 | 0.84-36.20 | 0.08 |

TABLE 4-continued

Relative odds for patients with metastasis associated with the risk score, patient's age and gender, tumor grade and size, and clinical stage in the testing cohort (n = 40).

|  | Met | Non-met | OR | 95% CI | P value |
|---|---|---|---|---|---|
| Size |  |  |  |  |  |
| ≤4 | 2 | 1 | — | — | — |
| >4-≤7 | 6 | 7 | 0.43 | 0.03-5.99 | 0.53 |
| >7 | 20 | 4 | 2.50 | 0.18-34.67 | 0.50 |
| Stage |  |  |  |  |  |
| I&II | 6 | 6 | — | — | — |
| III | 11 | 6 | 1.83 | 0.41-8.27 | 0.43 |
| IV | 11 | 0 | 1.16 | 0.00-∞ | 0.99 |

Met: patient with concurrent and subsequent metastasis;
Non-met: patient without metastasis.

Figure 4A:
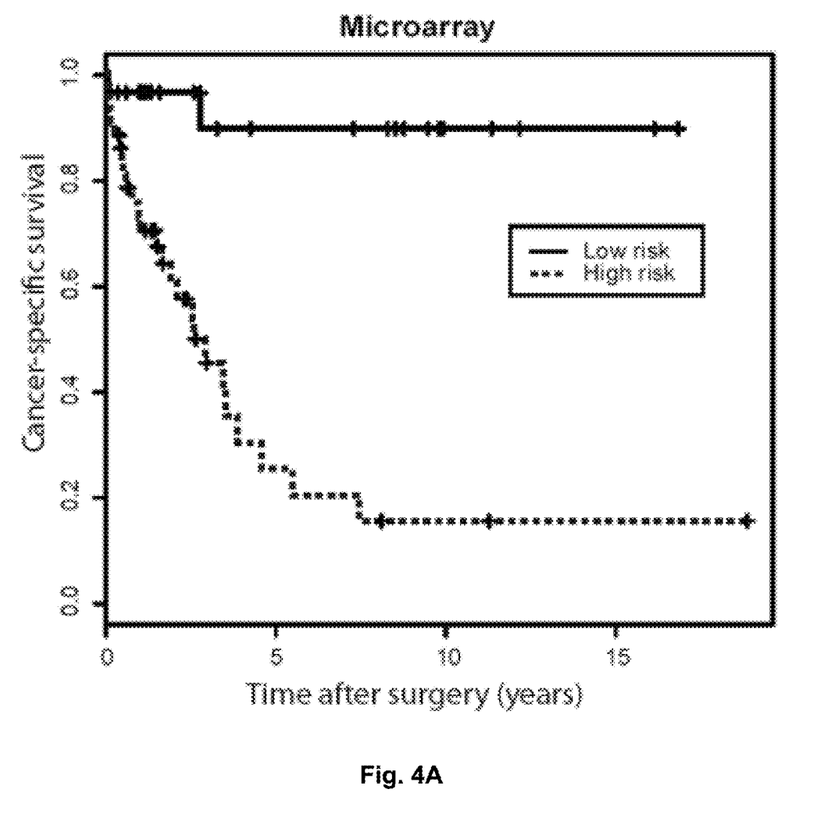
FIGS. 4A-B are a Kaplan-Meier analysis of cancer-specific survival in clear cell renal cell carcinoma (ccRCC) patients (all the training and testing cohort patients, n=68) stratified by the 4-miRNA signature using microarray (FIG. 4A) and quantitative PCR (qPCR) data (FIG. 4B).

Example 3: The 4-miRNA Expression Signature Predicts Overall Cancer-Specific Survival The miRNA expression was also examined to determine whether the expression signature model could independently predict the cancer-specific survival of ccRCC patients. With patients in the combined training and testing cohorts (n=68), a univariate Cox regression analysis showed that the predicted risk status was a significant prognostic factor for the patient's cancer-specific survival (Table 5). As shown in Table 5 below, relative risk for patients predicted to be of high risk was significantly higher as compared to patients of low risk (HR=12.68, 95% CI=2.97-54.13, p<0.0001). The stage of disease was the only other significant prognostic factor, while age, gender, tumor grade and size were not associated with survival. Patients predicted to be of high risk had a 5-year survival rate of only 32%, whereas those of low risk had a 5-year survival rate of 84% (FIG. 4A).

TABLE 5

Univariate Cox regression analysis of all patients (n = 68).

|  | HR | 95% CI | P value (Wald test) |
|---|---|---|---|
| Risk status (high vs low) |  |  |  |
| microarray | 12.68 | 2.97-54.13 | <0.0001 |
| quantitative PCR | 8.80 | 2.62-29.58 | <0.0001 |
| Age |  |  |  |
| 51-60 vs ≤50 | 1.35 | 0.50-3.66 | 0.56 |
| 61-70 vs ≤50 | 0.89 | 0.31-2.56 | 0.84 |
| >70 vs ≤50 | 0.54 | 0.11-2.60 | 0.44 |
| Age (continuous) | 0.98 | 0.95-1.01 | 0.17 |
| Gender (male vs female) | 1.70 | 0.74-3.91 | 0.21 |
| Grade* |  |  |  |
| III vs I&II | 2.67 | 0.80-8.89 | 0.11 |
| IV vs I&II | 2.52 | 0.67-9.42 | 0.17 |
| Stage |  |  |  |
| III vs I&II | 4.67 | 1.15-18.95 | 0.03 |
| IV vs I & II | 12.82 | 3.71-44.23 | <0.001 |
| Size* |  |  |  |
| 4-7 vs ≤4 | 4.36 | 0.51-37.31 | 0.18 |
| >7 vs ≤4 | 6.93 | 0.89-53.84 | 0.06 |

*The tumor grade and size are only applied to the primary tumors.

Figure 6A:
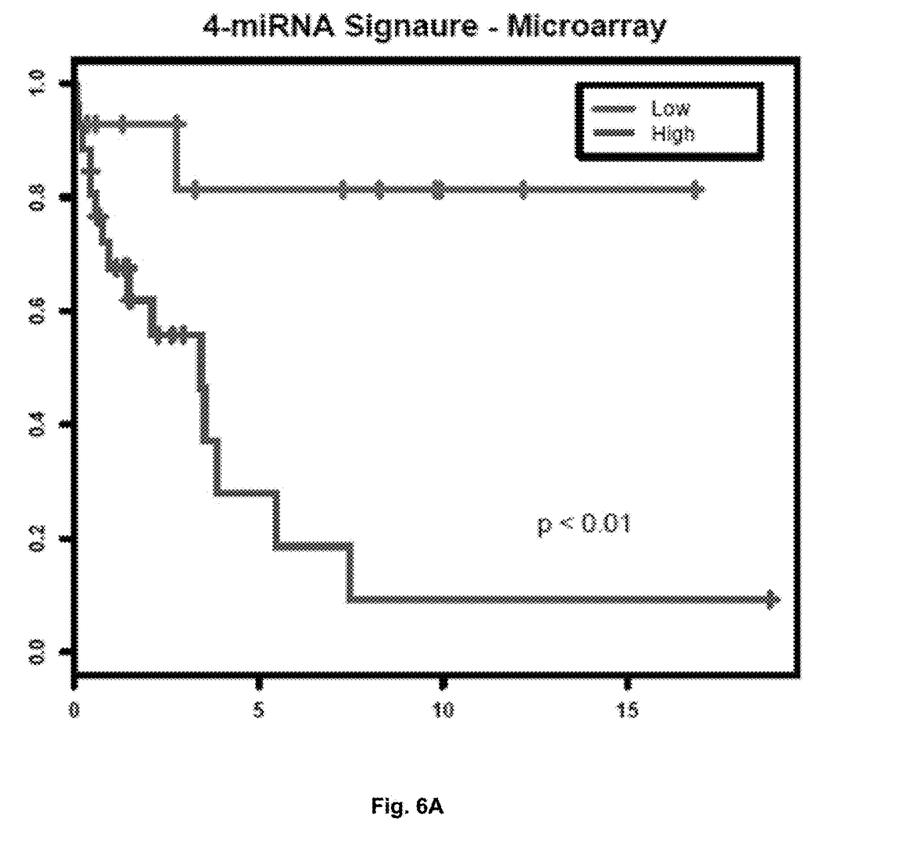
FIGS. 6A-C are a Kaplan-Meier analysis of cancer-specific survival in clear cell renal cell carcinoma (ccRCC) patients. They are all the testing cohort patients who are stratified by the 4-miRNA signature using microarray (n=40) (FIG. 6A) and quantitative PCR (qPCR) (n=40) (FIG. 6B), and by the UCLA Integrated Staging System (UISS) (n=35) (FIG. 6C). (low: low risk group; high: high risk group; intermediate: intermediate risk group.).
Figure 6B:
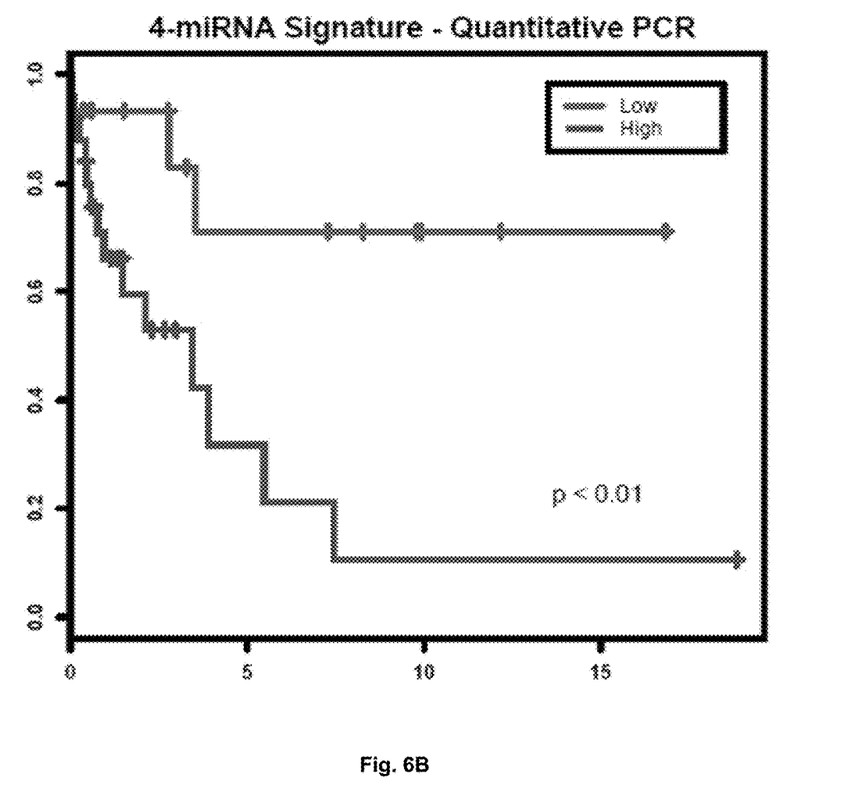
Figure 6C:
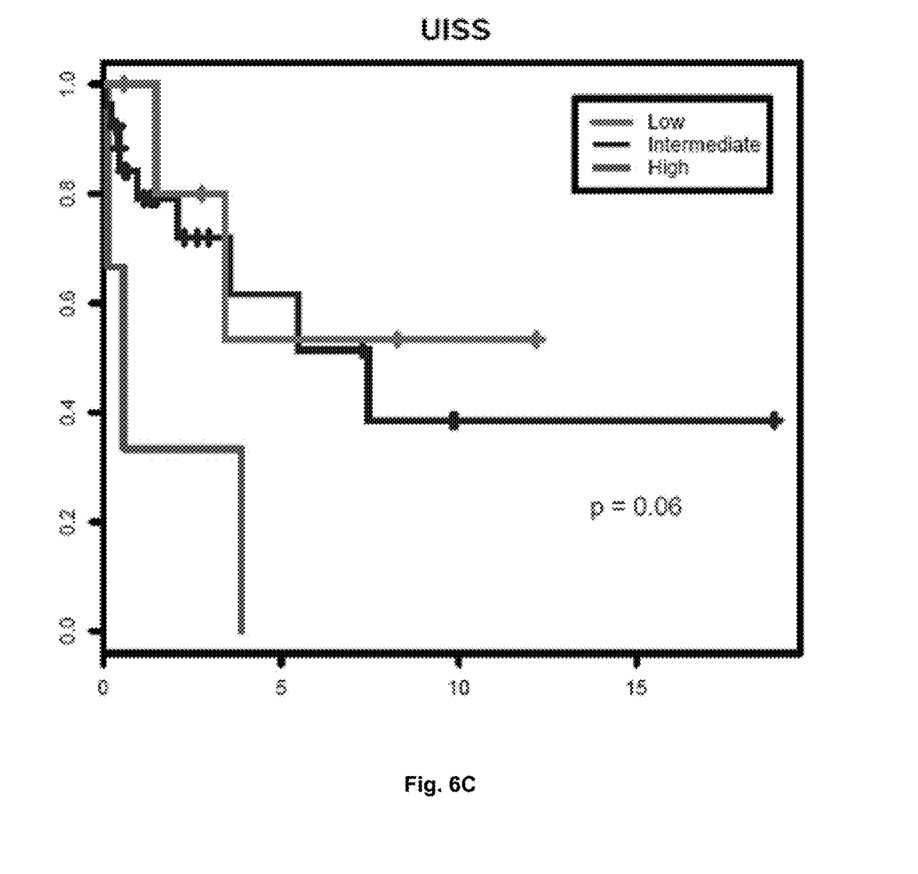

Currently, the UCLA Integrated Staging System (UISS) is a widely used prognostic tool for RCC patient outcome. UISS classifies cases into high, intermediate and low risk groups, based on tumor stage, histological grade and Eastern Cooperative Oncology Group (ECOG) performance status (PS) (Han et al. 2003). As reported in international multi-center studies (Han et al., 2003; Patard et al. 2004), the overall 5-year cancer-specific survival rates estimated by the UISS were 92-94%, 65-78% and 30-48% for the low, intermediate and high risk group patients, respectively. To directly compare the UISS system with the miRNA expression signature described herein, a UISS risk score to each of the testing cohort patients was assigned. The predicted 5-year cancer-specific survival rates were 0%, 63% and 52% for the high, intermediate and low risk group patients, respectively, by UISS, compared to 32% and 84% for the high and low risk patients, respectively, by the 4-miRNA expression signature (FIG. 6A-C). The UISS score is not a significant prognostic factor for the test cohort, but the risk scores based on both microarray and RT-PCR are statistically significant as shown in Table 6 below. The hazard ratio of high versus low risk status is 6.81 (95% CI=1.52-30.53, p value <0.01) and 4.88 (95% CI=1.37-17.38, p value <0.01), by microarray and qPCR, respectively. The miRNA expression signature developed from the current study has the potential to be applied in a routine clinical setting. A PCR-based test will make the expression signature assay more practical for a clinical laboratory usage.

TABLE 6

Univariate Cox regression analysis of patients in the testing cohort (n = 40)

|  | HR | 95% CI | P value (Wald test) |
|---|---|---|---|
| Risk status (high vs low) |  |  |  |
| microarray | 6.81 | 1.52-30.52 | 0.01 |
| quantitative PCR | 4.88 | 1.37-17.38 | 0.01 |
| UISS risk status* |  |  |  |
| high vs low | 5.60 | 0.90-34.88 | 0.07 |
| intermediate vs low | 1.45 | 0.31-6.77 | 0.63 |

*Five patients' UISS risk scores were not available (n = 35).

Example 4: Development of an RT-PCR Based 4-miRNA Expression Signature Assay One of the challenges of performing an RT-PCR based tissue miRNA expression analysis is to find a reliable reference miRNA or small RNA for the test normalization. To further develop a 4-miRNA expression signature assay using a RT-PCR platform, the microarray database of miRNA expression in all of the benign and tumor kidney samples (n=78) was analyzed.

After carefully analyzing the microarray data discussed herein, it was found that miR-24 was most constantly and stably expressed (Table 7). The 4-miRNA expression signature based on qPCR data also showed a high sensitivity (75%) and specificity (100%), as well as a similar association with cancer-specific death. This further validates the microarray results as and provides the technologic basis for a larger scale q-PCR based validation.

TABLE 7

Top 10 miRNAs with the least CV in expression of tumor and benign kidney tissue (n = 78).

| miRNA ID | SD | Mean | CV |
|---|---|---|---|
| hsa-miR-24 | 0.49 | 14.29 | 3.43% |
| hsa-miR-27a | 0.54 | 14.32 | 3.77% |
| hsa-miR-26a | 0.53 | 13.93 | 3.80% |
| hsa-miR-21 | 0.68 | 16.93 | 4.02% |
| hsa-miR-23a | 0.62 | 14.61 | 4.24% |
| hsa-miR-30b | 0.59 | 13.15 | 4.49% |
| hsa-miR-103 | 0.60 | 12.86 | 4.67% |
| hsa-miR-331-3p | 0.53 | 11.13 | 4.76% |
| hsa-miR-29a | 0.72 | 14.75 | 4.88% |
| hsa-miR-23b | 0.71 | 13.35 | 5.32% |

SD: standard deviation;
CV: coefficient of variation.

Figure 3B:
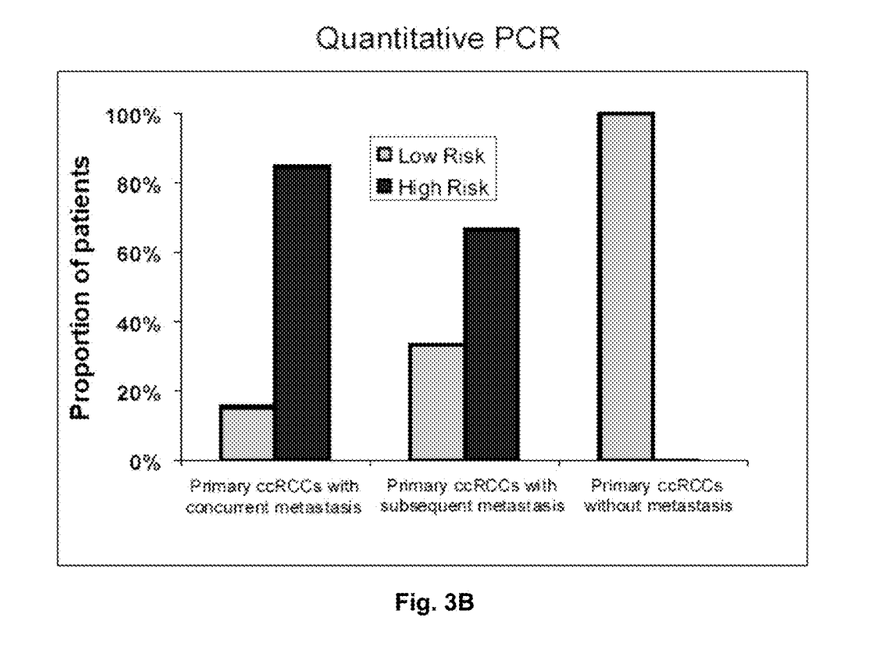
Figure 4B:
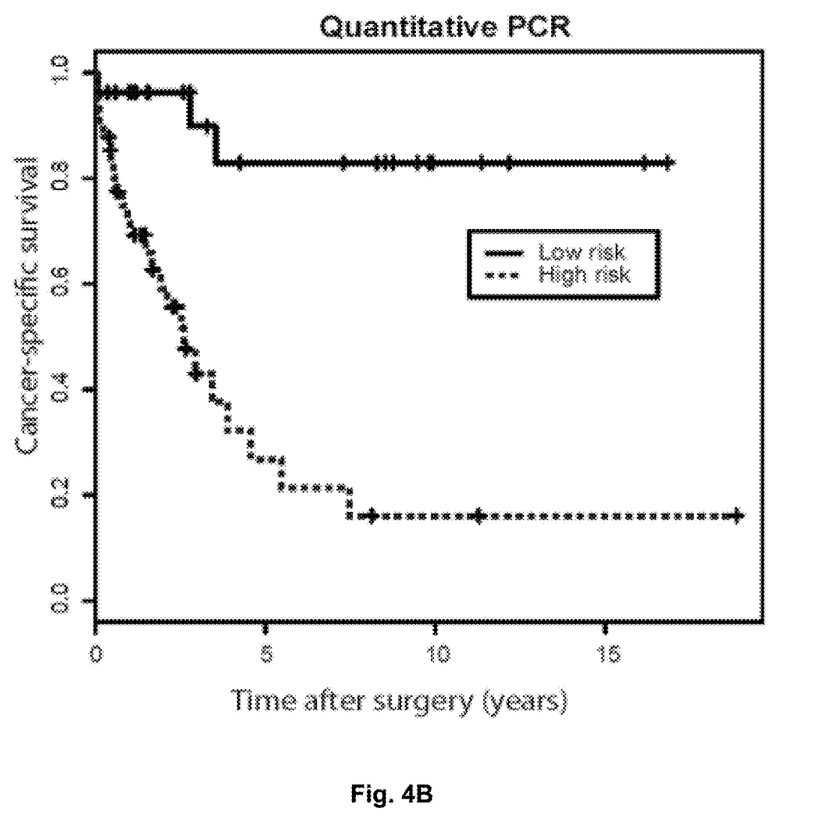

Therefore, miR-24 was selected as a reference miRNA for normalization. Each of the 4 miRNAs selected for the expression signature in each specimen in the training and testing cohorts were used, and their expression, normalized by that of miR-24, was analyzed using ABI TaqMan MicroRNA Assay. Similar to the microarray study described above, a PCR-based risk score formula model (Risk score=$1.431559 \times X_{miR-10b} - 1.530509 \times X_{miR-130b} + 1.888144 \times X_{miR-139-5p} - 2.569280 \times X_{miR-199b-5p}$) was constructed using the training cohort and the corresponding high risk cut-off score (−18.11) was determined (FIG. 2B). The expression signature was then validated using the testing cohort, which showed that 11 of 13 (85%) primary ccRCCs with concurrent metastasis and 10 of 15 (67%) localized tumors with subsequent metastasis were predicted to be of high risk, and 6 of 6 (100%) without metastasis were predicted to be of low risk (FIG. 3B). Overall, the validation test showed that the PCR-based assay of the expression signature had a sensitivity of 75% and a specificity of 100%. The findings were very similar to those based on the microarray platform. The expression signature was also found to be significantly associated with cancer-specific survival (HR=8.8, 95% CI=2.62-29.58, p<0.0001) (FIG. 4B, Table 5).

REFERENCES

The references listed below and all referenced cited above are hereby incorporated by reference in their entirety as if fully set forth herein.

1. Gupta K, Miller J D, Li J Z, Russell M W, Charbonneau C. Epidemiologic and socioeconomic burden of metastatic renal cell carcinoma (mRCC): a literature review. Cancer Treat Rev. 2008 May; 34(3):193-205.
2. Rini B I, Campbell S C, Escudier B. Renal cell carcinoma. Lancet. 2009 Mar. 28; 373(9669):1119-32.
3. Landis S H, Murray T, Bolden S, Wingo P A. Cancer statistics, 1999. C A: a cancer journal for clinicians. 1999 January-February; 49(1):8-31, 1.
4. Weinberg R A. Leaving home early: reexamination of the canonical models of tumor progression. Cancer cell. 2008 Oct. 7; 14(4):283-4.
5. Klein C A. Cancer. The metastasis cascade. Science. 2008 Sep. 26; 321(5897):1785-7.
6. Caroline Coghlin G I M. Current and emerging concepts in tumour metastasis. The Journal of pathology. 2010; 222(1):1-15.
7. Bartel D P. MicroRNAs: genomics, biogenesis, mechanism, and function. Cell. 2004 Jan. 23; 116(2):281-97.
8. Michael M Z, S M O C, van Hoist Pellekaan N G, Young G P, James R J. Reduced accumulation of specific microRNAs in colorectal neoplasia. Mol Cancer Res. 2003 October; 1(12):882-91.

9. Calin G A, Liu C G, Sevignani C, Ferracin M, Felli N, Dumitru C D, et al. MicroRNA profiling reveals distinct signatures in B cell chronic lymphocytic leukemias. Proceedings of the National Academy of Sciences of the United States of America. 2004 Aug. 10; 101(32):11755-60.
10. Calin G A, Ferracin M, Cimmino A, Di Leva G, Shimizu M, Wojcik S E, et al. A MicroRNA signature associated with prognosis and progression in chronic lymphocytic leukemia. The New England journal of medicine. 2005 Oct. 27; 353(17):1793-801.
11. Chan J A, Krichevsky A M, Kosik K S. MicroRNA-21 is an antiapoptotic factor in human glioblastoma cells. Cancer research. 2005 Jul. 15; 65(14):6029-33.
12. Iorio M V, Ferracin M, Liu C G, Veronese A, Spizzo R, Sabbioni S, et al. MicroRNA gene expression deregulation in human breast cancer. Cancer research. 2005 Aug. 15; 65(16):7065-70.
13. Eis P S, Tam W, Sun L, Chadburn A, Li Z, Gomez M F, et al. Accumulation of miR-155 and BIC RNA in human B cell lymphomas. Proceedings of the National Academy of Sciences of the United States of America. 2005 Mar. 8; 102(10):3627-32.
14. Yanaihara N, Caplen N, Bowman E, Seike M, Kumamoto K, Yi M, et al. Unique microRNA molecular profiles in lung cancer diagnosis and prognosis. Cancer cell. 2006 March; 9(3):189-98.
15. Cummins J M, Velculescu V E. Implications of microRNA profiling for cancer diagnosis. Oncogene. 2006 Oct. 9; 25(46):6220-7.
16. Metzler M, Wilda M, Busch K, Viehmann S, Borkhardt A. High expression of precursor microRNA-155/BIC RNA in children with Burkitt lymphoma. Genes, chromosomes & cancer. 2004 February; 39(2):167-9.
17. He L, Thomson J M, Hemann M T, Hernando-Monge E, Mu D, Goodson S, et al. A microRNA polycistron as a potential human oncogene. Nature. 2005 Jun. 9; 435 (7043):828-33.
18. Esquela-Kerscher A, Slack F J. Oncomirs—microRNAs with a role in cancer. Nature reviews. 2006 April; 6(4):259-69.
19. Calin G A, Croce C M. MicroRNA-cancer connection: the beginning of a new tale. Cancer research. 2006 Aug. 1; 66(15):7390-4.
20. Nicoloso M S, Spizzo R, Shimizu M, Rossi S, Calin G A. MicroRNAs—the micro steering wheel of tumour metastases. Nature reviews. 2009 April; 9(4):293-302.
21. Hurst D R, Edmonds M D, Welch D R. Metastamir: the field of metastasis-regulatory microRNA is spreading. Cancer research. 2009 Oct. 1; 69(19):7495-8.
22. Calin G A, Croce C M. MicroRNA signatures in human cancers. Nature reviews. 2006 November; 6(11):857-66.
23. Volinia S, Calin G A, Liu C G, Ambs S, Cimmino A, Petrocca F, et al. A microRNA expression signature of human solid tumors defines cancer gene targets. Proceedings of the National Academy of Sciences of the United States of America. 2006 Feb. 14; 103(7):2257-61.
24. Yu S L, Chen H Y, Chang G C, Chen C Y, Chen H W, Singh S, et al. MicroRNA signature predicts survival and relapse in lung cancer. Cancer cell. 2008 January; 13(1):48-57.
25. Cervigne N K, Reis P P, Machado J, Sadikovic B, Bradley G, Galloni N N, et al. Identification of a microRNA signature associated with progression of leukoplakia to oral carcinoma. Hum Mol Genet. 2009 Dec. 15; 18(24):4818-29.
26. Patnaik S K, Kannisto E, Knudsen S, Yendamuri S. Evaluation of microRNA expression profiles that may predict recurrence of localized stage I non-small cell lung cancer after surgical resection. Cancer research. 2010 Jan. 1; 70(1):36-45.
27. Hiroki E, Akahira J, Suzuki F, Nagase S, Ito K, Suzuki T, et al. Changes in microRNA expression levels correlate with clinicopathological features and prognoses in endometrial serous adenocarcinomas. Cancer science. 2010 January; 101(1):241-9.
28. Weng L, Wu X, Gao H, Mu B, Li X, Wang J H, et al. MicroRNA profiling of clear cell renal cell carcinoma by whole-genome small RNA deep sequencing of paired frozen and formalin-fixed, paraffin-embedded tissue specimens. The Journal of pathology. 2010 May 21.
29. Simon R, Radmacher M D, Dobbin K, McShane L M. Pitfalls in the use of DNA microarray data for diagnostic and prognostic classification. J Natl Cancer Inst. 2003 Jan. 1; 95(1):14-8.
30. Cohen H T, McGovern F J. Renal-cell carcinoma. The New England journal of medicine. 2005 Dec. 8; 353(23): 2477-90.
31. Nakada C, Matsuura K, Tsukamoto Y, Tanigawa M, Yoshimoto T, Narimatsu T, et al. Genome-wide microRNA expression profiling in renal cell carcinoma: significant down-regulation of miR-141 and miR-200c. The Journal of pathology. 2008 December; 216(4):418-27.
32. Chow T F, Youssef Y M, Lianidou E, Romaschin A D, Honey R J, Stewart R, et al. Differential expression profiling of microRNAs and their potential involvement in renal cell carcinoma pathogenesis. Clin Biochem. 2010 January; 43(1-2):150-8.
33. Jung M, Mollenkopf H J, Grimm C, Wagner I, Albrecht M, Waller T, et al. MicroRNA profiling of clear cell renal cell cancer identifies a robust signature to define renal malignancy. Journal of cellular and molecular medicine. 2009 September; 13(9B):3918-28.
34. Guo J, Miao Y, Xiao B, Huan R, Jiang Z, Meng D, et al. Differential expression of microRNA species in human gastric cancer versus non-tumorous tissues. J Gastroenterol Hepatol. 2009 April; 24(4):652-7.
35. Borgdorff V, Lleonart M E, Bishop C L, Fessart D, Bergin A H, Overhoff M G, et al. Multiple microRNAs rescue from Ras-induced senescence by inhibiting p21 (Waf1/Cip1). Oncogene. 2010 Apr. 15; 29(15):2262-71.
36. Garzia L, Andolfo I, Cusanelli E, Marino N, Petrosino G, De Martino D, et al. MicroRNA-199b-5p impairs cancer stem cells through negative regulation of HES1 in medulloblastoma. PLoS one. 2009; 4(3):e4998.
37. Sasayama T, Nishihara M, Kondoh T, Hosoda K, Kohmura E. MicroRNA-10b is overexpressed in malignant glioma and associated with tumor invasive factors, uPAR and RhoC. International journal of cancer. 2009 Sep. 15; 125(6):1407-13.
38. Tian Y, Luo A, Cai Y, Su Q, Ding F, Chen H, et al. MicroRNA-10b promotes migration and invasion through KLF4 in human esophageal cancer cell lines. The Journal of biological chemistry. 2010 Mar. 12; 285(11):7986-94.
39. Ma L, Teruya-Feldstein J, Weinberg R A. Tumour invasion and metastasis initiated by microRNA-10b in breast cancer. Nature. 2007 Oct. 11; 449(7163):682-8.
40. Gee H E, Camps C, Buffa F M, Colella S, Sheldon H, Gleadle J M, et al. MicroRNA-10b and breast cancer metastasis. Nature. 2008 Oct. 23; 455(7216):E8-9; author reply E.
41. Jiang Z, Chu P G, Woda B A, Rock K L, Liu Q, Hsieh C C, et al. Analysis of RNA-binding protein IMP3 to predict metastasis and prognosis of renal-cell carcinoma: a retrospective study. Lancet Oncol. 2006 July; 7(7):556-64.
42. Han K R, Bleumer I, Pantuck A J, Kim H L, Dorey F J, Janzen N K, et al. Validation of an integrated staging system toward improved prognostication of patients with localized renal cell carcinoma in an international population. J Urol. 2003 December; 170(6 Pt 1):2221-4.
43. Patard J J, Kim H L, Lam J S, Dorey F J, Pantuck A J, Zisman A, et al. Use of the University of California Los Angeles integrated staging system to predict survival in renal cell carcinoma: an international multicenter study. J Clin Oncol. 2004 Aug. 15; 22(16):3316-22.
44. Peltier H J, Latham G J. Normalization of microRNA expression levels in quantitative R T-PCR assays: identification of suitable reference RNA targets in normal and cancerous human solid tissues. RNA (New York, N.Y. 2008 May; 14(5):844-52.

What is claimed is:

1. A method for predicting existence of or risk for developing metastasis in a renal cell carcinoma comprising:
    detecting a test expression level of a set of one or more miRNAs of a renal cell carcinoma-specific expression signature comprising miR-10b, miR-139-5p, miR-130b, and miR-199b-5p in a biological sample from a subject having a renal cell cancer;
    assigning a risk score to the test expression level, wherein the risk score is calculated by a formula:

$$\text{Risk score} = -1.275564 \times X_{miR-10b} + 2.106701 \times X_{miR-130b} - 2.278192 \times X_{miR-139-5p} + 1.101139 \times X_{miR-199b-5p}; \text{ and}$$

predicting the existence of or a high risk for developing metastasis when the test expression level is assigned a high risk score, predicting a low risk for developing metastasis when the test expression level is assigned a low risk score.

2. The method of claim 1, wherein the test expression level is determined by microarray.

3. The method of claim 1, wherein the test expression level is determined by RT-PCR.

4. The method of claim 1, wherein the renal cell carcinoma is clear cell renal cell carcinoma.

5. The method of claim 1, wherein the prognosis is overall cancer survival.

* * * * *